United States Patent
Hartley et al.

(10) Patent No.: US 7,112,197 B2
(45) Date of Patent: Sep. 26, 2006

(54) SURGICAL DEVICE WITH PRESSURE MONITORING ABILITY

(75) Inventors: Amanda April Hartley, Brampton (CA); Krishan Shah, Mississauga (CA); Naheed Visram, Markham (CA)

(73) Assignee: Baylis Medical Company Inc., Montreal (CA)

( * ) Notice: Subject to any disclaimer, the term of this patent is extended or adjusted under 35 U.S.C. 154(b) by 149 days.

(21) Appl. No.: 10/347,366

(22) Filed: Jan. 21, 2003

(65) Prior Publication Data

US 2004/0143261 A1    Jul. 22, 2004

(51) Int. Cl.
    *A61B 18/18*    (2006.01)
    *A61B 5/02*    (2006.01)

(52) U.S. Cl. ........................................ 606/41; 600/485

(58) Field of Classification Search ............ 606/32–50; 600/485–488

See application file for complete search history.

(56) References Cited

U.S. PATENT DOCUMENTS

| | | | |
|---|---|---|---|
| 3,448,739 A | 6/1969 | Stark et al. | |
| 4,682,596 A | 7/1987 | Bales et al. | |
| 4,928,693 A | 5/1990 | Goodin et al. | |
| 4,936,281 A | 6/1990 | Stasz | |
| 5,098,431 A | 3/1992 | Rydell | |
| 5,281,216 A * | 1/1994 | Klicek ........................ | 606/42 |
| 5,364,393 A | 11/1994 | Auth et al. | |
| 5,403,338 A | 4/1995 | Milo | |
| 5,683,366 A | 11/1997 | Eggers et al. | |
| 5,893,848 A * | 4/1999 | Negus et al. ................. | 606/41 |
| 5,904,679 A | 5/1999 | Clayman | |
| 5,921,957 A | 7/1999 | Killion et al. | |
| 6,293,945 B1 | 9/2001 | Parins et al. | |
| 6,296,615 B1 | 10/2001 | Brockway et al. | |
| 6,565,562 B1 * | 5/2003 | Shah et al. ................... | 606/41 |
| 6,650,923 B1 | 11/2003 | Lesh et al. | |
| 6,811,544 B1 * | 11/2004 | Schaer ..................... | 604/95.04 |
| 6,814,733 B1 | 11/2004 | Schwartz et al. | |
| 2002/0087156 A1 * | 7/2002 | Maguire et al. .............. | 606/41 |
| 2002/0123749 A1 * | 9/2002 | Jain ............................ | 606/41 |
| 2002/0169377 A1 | 11/2002 | Khairkhahan et al. | |

FOREIGN PATENT DOCUMENTS

| | | |
|---|---|---|
| WO | WO-93/20747 | 10/1993 |
| WO | WO-04039433 | 5/2004 |

OTHER PUBLICATIONS

Kamal K. Sethi, Jagdish C. Mohan. "Editiorial Comment: Transseptal Catheterization for the Electrophysiologist: Modification with a 'View'". Journal of Interventional Cardian Physiology. 5, 97-99, 2001.

(Continued)

*Primary Examiner*—Michael Peffley

(57) ABSTRACT

A device with a functional tip containing at least one active electrode capable of creating a controlled perforation in body tissue through the application of Radio Frequency (RF) energy is described. The position of the tip of the device can be determined in response to pressure sensed at the tip and determined by a monitor. The device is useful to remove or perforate unwanted tissue in a controlled manner in any location in the body, particularly in the atrial septum for controlled transseptal puncture. In this application, the device is introduced into the right atrium, and the functional tip is then positioned against the atrial septum. Energy is applied to create the perforation and pressure is monitored to determine if the perforation was created in a desired location. Other possible applications include the removal of plaque or thrombotic occlusions from diseased vessels.

38 Claims, 9 Drawing Sheets

OTHER PUBLICATIONS

Christodoulos Stefanadis. "Retrograde Nontransseptal Balloon Mitral Valvuloplasty: Immediate Results and Intermediate Long-Term Outcome in 441 Cases—A Multicentre Experience". Journal of the American College of Cardiology. 32(4): 1009-16 (1998).

N. Shimko, P. Savard, K. Shah. "Radio frequency perforation of cardiac tissue: modelling and experimental results". Med. Biol. Eng. Comput. 38: 575-582 (2000).

Benson, Lee N., David Nykanen, Amanda Collison, "Radiofrequency Perforation in the Treatment of Congenital Heart Disease". *Catherizations and Cardiovascular Interventions;* 56: 72-82, 2002.

Conti C. R., "Transseptal Left Heart Catheterization for Radiofrequency Ablation of Accessory Pathways". *Clinical Cardiology;* 16: 367-368, 1993.

Justino, Henri, Lee N. Benson, David. G. Nykanen, "Transcatheter Creation of an Atrial Septal Defect Using Radiofrequency Perforation". *Catheterization and Cardiovascular Interventions;* 54: 83-87, 2001.

Sarvaas, Gideon J. Du Marchie, Kalyani R. Trivedi, Lisa K. Hornberger, K. Jin Lee, Hoel A. Kirsh, Lee N. Benson, "Radiofrequency-Assisted Atrial Septoplasty for an Intact Atrial Septum in Complex Congenital Heart Disease". *Catheterization and Cardiovascular Interventions;* 56: 412-415, 2002.

CA Pedra, LN de Sousa, SR Pedra, WP Ferreira, SL Braga, CA Esteves, MV Santant, JE Sousa, VF Fortes. "New Percutaneous techniques for perforating the pulmonary valve in pulmonary atresia with intact ventricular septum", Arq Bras Cariol. 77(5):471-48 (2001).

DG Nykanen, J Phikala, GP Taylor, LN Benson. "Radiofrequency assisted perforation of the atrial septum in a swine model: feasibility, biophysical and histological characteristics", Circulation. 100(Suppl 1):I-804 (1999).

Baylis Medical Company Inc., "Radio Frequency Perforation System", 2001.

"ABSTRACT of European Patent No. 0315730 to Osypka", (1989).

* cited by examiner

SURGICAL DEVICE WITH PRESSURE MONITORING ABILITY

TECHNICAL FIELD

The invention relates to a surgical device and method with pressure monitoring ability. More specifically, the invention relates to a device and method for creating a controlled perforation in the atrial septum while monitoring blood pressure.

BACKGROUND OF THE ART

Electrosurgical devices perforate or cut tissues when radio frequency (RF) electrical energy rapidly increases tissue temperature to the extent that the intracellular fluid becomes converted to steam, inducing cell lysis as a result of elevated pressure within the cell. The radio frequency range lies between 10 kHz and 300 MHz, but electrosurgical devices usually operate at a frequency between 400 kHz and 550 kHz. This technology can be used to create perforations in different types of tissue, such as heart tissue, vascular occlusions, and others. Commonly, RF devices are described for use in perforating vascular occlusions. A device to dilate and/or lance blood vessels that are morbidly contracted or clogged is described in European Patent Application Number EP 0315730, of Osypka, published May 15, 1989. This device describes the use of RF energy in either bipolar or monopolar application modes to open blood vessels by means of heat. Other devices intended to use RF energy to pass through occluded vessels have also been described (U.S. Pat. No. 5,364,393, of Auth et al., issued Nov. 15, 1994, WO 93/20747, publication of PCT Patent Application No. PCT/US93/03759, of Rosar, published Oct. 28, 1993, U.S. Pat. No. 5,098,431, of Rydell, issued Mar. 24, 1992, and U.S. Pat. No. 4,682,596 of Bales et al., issued Jul. 28, 1987). U.S. Pat. No. 6,293,945 B1, of Parins et al., issued Sep. 25, 2001 describes an electrosurgical instrument with suction capability. This device has three functions at the tip including cutting, coagulating, and suction. None of these devices however incorporate a means for verifying the location of the device within the body. One means for verifying location is described in U.S. Pat. No. 4,936,281, of Stasz, issued Jun. 26, 1990, which describes an ultrasonically enhanced RF catheter used for cutting. An ultrasonic transducer connected to an electronics module receives echo signals, enabling Doppler flow readings and ultrasound imaging of the vessel.

Having reliable information about the location of electrosurgical devices within a body is an important aid to performing a successful procedure. It is often valuable to have more than one source of this information because every imaging technique has limitations, and using only one method can lead to erroneous information. Relative blood pressure measurements can be a useful tool to verify the position of a device in a body. Different locations in the body are known to have characteristic blood pressure ranges. Knowing the blood pressure at the tip of a perforation device is a useful tool to determine the location of the device, particularly in instances where imaging techniques provide inconclusive information. A device that is used for measuring pressure in coronary arteries is described in U.S. Pat. No. 4,928,693, of Goodin et al., issued May 29, 1990; however the device is not capable of perforating tissue using RF energy. U.S. Pat. No. 6,296,615 B1, of Brockway et al., issued Oct. 2, 2001, describes a catheter with a physiological sensor. This catheter consists of a pressure transducer for monitoring pressure, as well as the ability to detect and/or transmit an electrical signal.

It is often required to create a perforation in the atrial septum to gain access to the left side of the heart interventionally to study or treat electrical or morphological abnormalities. It is also often desirable to create a hole in the septum in order to shunt the blood flow between the left and right sides of the heart to relieve high pressure or provide more blood flow to certain areas. Historically in these instances, a stiff needle such as the Transseptal needle set of Cook Incorporated, Bloomington, Ind., USA is introduced through a guiding sheath in the femoral vein and advanced through the vasculature into the right atrium. From there the needle tip is positioned at the fossa ovalis, the preferred location on the septum for creating a hole. Once in position, mechanical energy is used to advance the needle through the septum and into the left atrium. Once in the left atrium the needle can be attached to a pressure transducer and the operator can confirm a left atrial pressure before continuing with the procedure. Examples of subsequent steps may include advancing the guiding sheath over the needle and into the left atrium to provide access for other devices to the left heart, or using another device to enlarge the hole made by the needle if a shunt is desired.

Another device and method for creating a transseptal puncture is described in U.S. Pat. No. 5,403,338, of Milo, issued Apr. 4, 1995, which describes a punch that is intended to create an opening between two compartments. This device also makes use of mechanical energy, as with the transseptal needle.

These methods of creating a transseptal perforation rely on the skill of the operator and require practice to be performed successfully. The needles used in this procedure are very stiff and can damage the vessel walls as they are being advanced. In addition, the amount of force required to perforate the septum varies with each patient. If too much force is applied there is the possibility of perforating the septum and continuing to advance the needle so far that damage is done to other areas of the heart. C. R. Conti (1993) discusses this possibility, and states that if the operator is not careful, the posterior wall of the heart can be punctured by the needle when it crosses the atrial septum because of the proximity of the two structures. It can also be difficult to position the needle appropriately in hearts that have malformations, or an a typical orientation. Justino et al. (2001) note that despite improvements to the technique with the needle since its first introduction, most large series continue to report failed or complicated mechanical transseptal punctures, for reasons such as unusual septal thickness, or contour. Patients with a muscular septum, as well as those with a thick septum can benefit from an alternative to the transseptal needle puncture (Benson et al, 2002), as it is difficult to control the amount of mechanical force required to create the puncture. Furthermore, children born with heart defects such as hypoplastic left heart syndrome could benefit from an alternative technique. The abnormal anatomy of these patients including a small left atrium increases the likelihood of injury or laceration of surrounding structures during transseptal puncture (Sarvaas, 2002). The patient population discussed above would benefit from a device and technique for transseptal puncture that allows for a more controlled method of perforation and a method to confirm that the perforation has been made in the correct location.

SUMMARY OF THE INVENTION

It is an object of the invention to provide a surgical device with pressure monitoring ability. It is a further object to provide a method of surgery involving determining a position of a surgical cutting device in response to pressure measured via the device.

In accordance with a first aspect of the invention, there is provided a surgical device for cutting material and monitoring pressure. The surgical device comprises an elongate member having a distal region and a proximal region. An energy delivery device is associated with the elongate member at the distal region for delivering cutting energy to the material and the energy delivery device is adapted for connection to an energy source. A pressure sensing mechanism is also associated with the distal region for monitoring pressure about the distal region.

The cutting energy is at least one form of energy selected from a group consisting of: electrical current; microwave; ultrasound; and laser. When the energy is electrical current, it may have a frequency within the radio frequency range. Further, when the material to be cut comprises cellular tissue, the energy delivery device is operable to deliver sufficient energy to the tissue to result in a rapid increase in the intracellular temperature causing vaporization of intracellular water and subsequent cell lysis.

In accordance with an embodiment of the first aspect, the pressure sensing mechanism comprises a pressure transmitting lumen extending between the proximal and distal regions. The lumen at the proximal region is adapted for fluid communication with a pressure transducer that provides a signal which varies as a function of pressure and adapted at the distal region for fluid communication with an environment about said distal region. In such an embodiment, the distal region may comprise at least one opening to the environment and the lumen is in fluid communication with the at least one opening.

In accordance with a further embodiment of the first aspect, the pressure sensing mechanism comprises a pressure transducer on-board the elongate member and associated with the distal region. The transducer is adapted for communication with a pressure monitoring system for monitoring pressure as a function of time.

The energy delivery device may comprise a functional tip with at least one active electrode. Further the energy delivery device may comprise a functional tip having two or more electrodes and the electrodes may be configured in an arrangement where at least one of the electrodes is active and at least one is a return electrode.

In accordance with a further aspect of the invention, there is provided a method of surgery. The method comprises introducing a surgical device into a body of a patient where the surgical device comprises a flexible elongate member having a distal region and a proximal region and an energy delivery device capable of cutting material and a pressure sensing mechanism for determining pressure in the body. The energy delivery device and pressure sensing mechanism are associated with the distal region. The surgical device is positioned to a first desired location in the patient's body where the energy delivery device is adjacent the material to be cut. Energy is delivered using the energy delivery device to cut the material. Pressure is measured in the body using the pressure sensing mechanism in order to determine the position of the surgical device at least one of before and after delivering energy to cut the material.

The method may further comprise advancing the device to a second desired location and measuring pressure using the pressure sensing mechanism at the second location. For example, the pressure measured at the second location may be blood pressure in the left atrium of the patient's heart.

The step of introducing may comprise introducing the device into the patient's vasculature and the material to be cut may be tissue located on an atrial septum of a heart.

As well, in an embodiment of the method, the step of introducing the device into the patient's vasculature comprises inserting the device into a guiding catheter positioned in the patient's vasculature.

In accordance with a further aspect of the invention there is provided an electrosurgical device comprising a flexible elongate member having a distal region and a proximal region where the distal region is insertable within and along a lumen within a body of a patient and maneuverable therethrough to a desired location where the device is operated to cut material and monitor pressure at the desired location. At least one electrode is associated with the distal region for cutting tissue and the at least one electrode is adapted for coupling to an electrical power source. A pressure sensing mechanism is associated with the distal region for sensing pressure at the desired location within the body and the mechanism is adapted for coupling to a pressure monitoring system.

Preferably, the pressure sensing mechanism is configured to minimize a portion of the elongate member that is necessary to be located at the desired location to monitor pressure.

The pressure sensing mechanism may comprises a pressure transmitting lumen defined within the elongate member extending from the proximal region to and through at least one opening defined in the distal region. The proximal region may be adapted for coupling the pressure transmitting lumen to a pressure transducer associated with the pressure monitoring system and the pressure transmitting lumen may be adapted for at least one of injecting a fluid to or removing a fluid from said body. The at least one electrode may be coupled to the energy source by a coupling means extending through the pressure transmitting lumen.

In accordance with yet another aspect of the invention, there is provided a surgical device comprising means for cutting material at a desired location in a body of a patient and means for determining a position of the device responsive to pressure within the body.

There is also provided a method of cutting tissue at a desired location in a body of a patient in accordance with the invention. The method comprises inserting a surgical device into the body where the surgical device comprising means for cutting material and means for determining a position of the device responsive to pressure within the body. The surgical device is positioned at the desired location in response to the means for determining a position of the device. The method may also comprise cutting material at the desired location and further comprise advancing the device in the body in response to said means for determining a position of the device. As well, the method may comprise re-positioning the device for re-cutting in response to the means for determining a position of the device.

It is to be understood that references to cut or cutting material such as tissue in relation to the present invention include perforating, ablating, coagulating and removing material.

DESCRIPTION OF THE DRAWINGS

In order that the invention may be readily understood, embodiments of the invention are illustrated by way of examples in the accompanying drawings, in which.

DETAILED DESCRIPTION OF THE INVENTION

Figure 1:
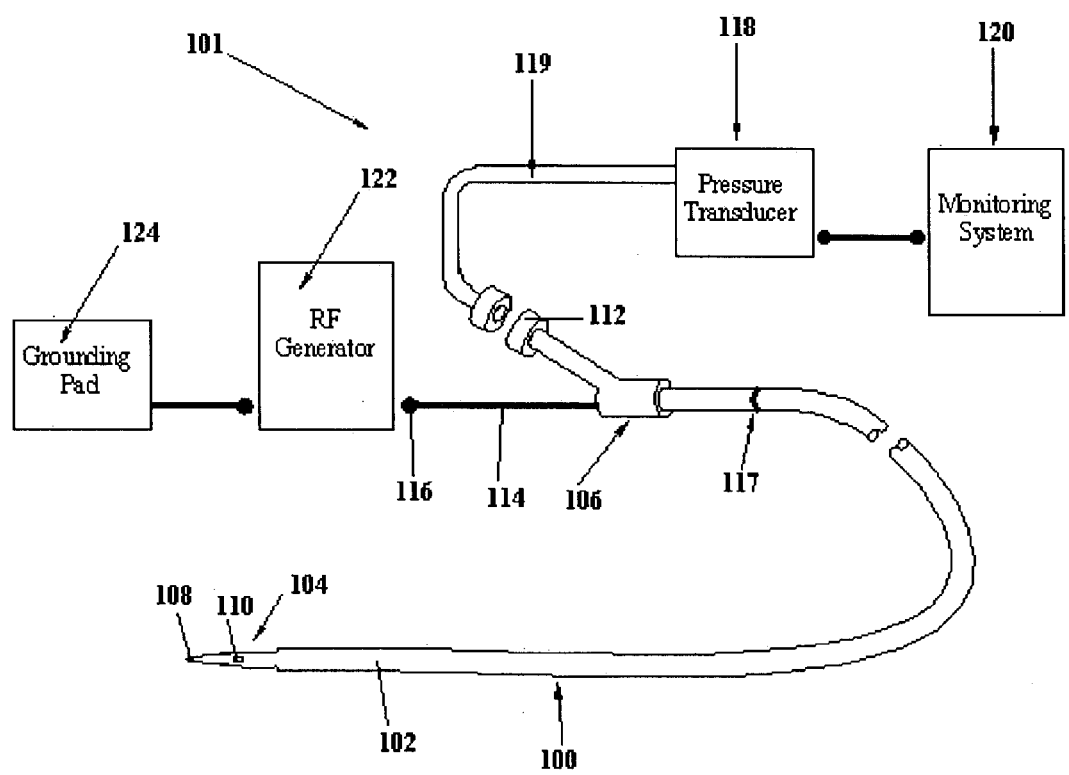
FIG. 1 illustrates a schematic view of an electrosurgical system including a preferred embodiment of an electrosurgical device in accordance with a preferred embodiment of the invention.

FIG. 1 illustrates a preferred embodiment of an electrosurgical perforation device 100 in accordance with the invention in an electrosurgical system 101. Device 100 comprises a flexible elongate member 102 having a distal region 104, and a proximal region 106. Distal region 104 is adapted to be inserted within and along a lumen of a body of a patient, such as a patient's vasculature, and maneuverable therethrough to a desired location proximate to material such as tissue to be cut.

Figure 2:
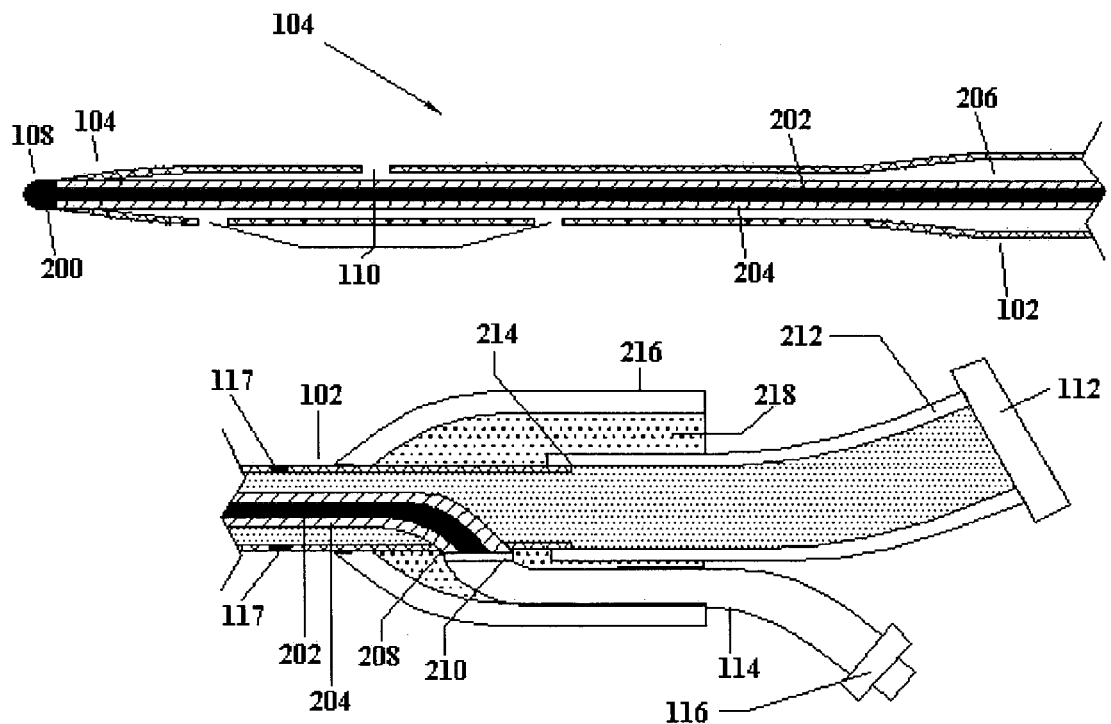
FIG. 2 illustrates a side cross-sectional view of the device of FIG. 1.

Elongate member 102 is typically tubular in configuration, having at least one lumen extending from proximal region 106 to distal region 104 such as lumen 206 shown in FIG. 2. Elongate member 102 is preferably constructed of a biocompatible polymer material that provides column strength to device 100. Member 102 is sufficiently stiff to permit a soft guiding sheath to be easily advanced over device 100 and through a perforation. Examples of suitable materials for the tubular portion of member 102 are polyetheretherketone (PEEK), and polyimide. In a preferred embodiment, the outer diameter of the tubular portion of member 102 tapers down to connect to distal region 104. In alternate embodiments the outer diameter of member 102 and the outer diameter of distal region 104 are the same.

Distal region 104 is constructed of a softer polymer material so that it is pliable and atraumatic when advanced through vasculature. An example of a suitable plastic is Pebax (a registered trademark of Atofina Chemicals, Inc.). Distal region 104 preferably has a smaller outer diameter than member 102 so that dilation of a perforation is limited while the distal region 104 is advanced through the perforation. Limiting dilation ensures that the perforation will not cause hemodynamic instability once device 100 is removed. The outer diameter of distal region 104 will preferably be no larger than 0.035" (0.897 mm). This is comparable to the distal outer diameter of the Brockenbrough transseptal needle that is traditionally used for creating a perforation in the atrial septum. Member 102 is preferably no larger than 0.050" (1.282 mm) which is also comparable to the transseptal needle dimensions.

Distal region 104 comprises an energy delivery device configured as a functional tip 108. Functional tip 108 comprises at least one active electrode made of a conductive and radiopaque material, such as stainless steel, tungsten, platinum, or another metal. A radiopaque marker (not shown) may be affixed to member 102 to highlight the location of the transition from distal region 104 to member 102, or other important landmarks on device 100. Distal region 104 defines at least one opening 110 in fluid communication with main lumen 206 (FIG. 2) as described further below.

Proximal region 106 comprises a hub 112, a cable 114, and a connector 116. Proximal region 106 may also have one or more markings 117 to indicate distances from functional tip 108, or other important landmarks on device 100. Hub 112 is configured to releaseably couple device 100 to an external pressure transducer 118 via external tubing 119. External pressure transducer 118 is coupled to a monitoring system 120 that converts a pressure signal from external pressure transducer 118 and displays pressure as a function of time. Cable 114 is coupled to connector 116 which is used to releaseably couple device 100 to an energy source such as a generator 122.

Generator 122 is preferably a radiofrequency (RF) electrical generator that is designed to work in a high impedance range. Because of the small size of functional tip 108 the impedance encountered during RF energy application is very high. General electrosurgical generators are typically not designed to deliver energy in these impedance ranges, so only certain RF generators can be used with this device. In the preferred embodiment, the energy is delivered as a continuous wave at a frequency between about 400 kHz and about 550 kHz. An appropriate generator for this application is the BMC RF Perforation Generator (model number RFP-100, Baylis Medical Company, Montreal, Canada). This generator delivers continuous RF energy at about 460 kHz. A grounding pad 124 is coupled to generator 122 for attaching to a patient to provide a return path for the RF energy. Other embodiments could use pulsed or non-continuous RF energy. In still other embodiments of the surgical device 100, different energy sources may be used, such as microwave, ultrasound, and laser with appropriate energy delivery coupling devices and energy delivery devices.

Referring to FIG. 2 a cross-section of device 100 is illustrated in accordance with the embodiment of FIG. 1. Functional tip 108 comprises an active electrode 200 that is coupled to an insulated conducting wire 202. Conducting wire 202 is preferably attached to distal region 104 using an adhesive. Alternately, distal region 104 is melted onto insulation 204 on conducting wire 202 to form a bond.

Figure 3:
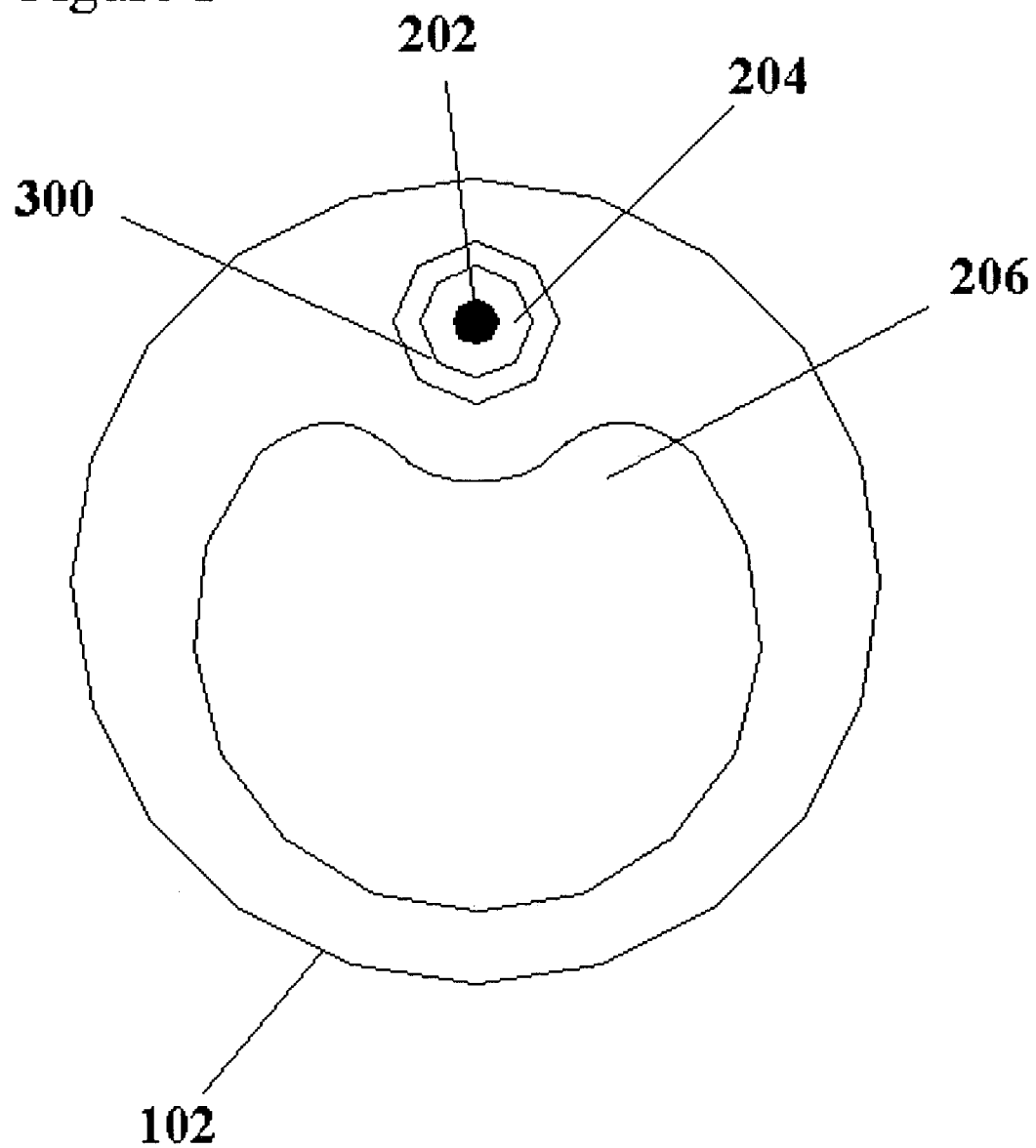
FIG. 3 illustrates a cross-sectional view of an alternate embodiment of the device.

Conducting wire 202 carries electrical energy from generator 122 to active electrode 200. Conducting wire 202 is covered with insulation 204 made of a biocompatible material that is able to withstand high temperatures such as polytetrafluoroethylene (PTFE), or other insulating material. Conducting wire 202 preferably extends through a main lumen 206 of device 100 which lumen extends from proximal region 106 to distal region 104. In an alternate embodiment, member 102 comprises main lumen 206 and a separate lumen 300. A cross section of the alternate embodiment is illustrated in FIG. 3. Separate lumen 300 contains the conducting wire 202 therein and main lumen 206 is used for aspiration of blood and injection of contrast and other media.

This embodiment of member 102 allows a dedicated lumen for each function of device 100.

In the preferred embodiment of FIG. 2, main lumen 206 extends from distal region 106 along member 102 and through distal region 104 of device 100. At least one opening 110 at the distal region 104 provides a pathway between main lumen 206 and the environment surrounding distal region 104, such as a desired location within a patient's body. Openings 110 are sufficiently dimensioned to easily aspirate blood to and through main lumen 206 and to inject radiopaque contrast; however, openings 110 are limited in number and dimension so that they do not compromise the structural integrity of distal region 104. The location of openings 110 is as close to functional tip 108 as possible so that only a small portion of device 100 is required to be proximate to the desired location for the determination of pressure.

Hub 112 is configured for releaseably coupling to an external pressure transducer 118, or a standard syringe. Preferably, hub 112 comprises a female Luer lock connection. Hub 112 is coupled to main lumen 206 via tubing 212 to provide a pathway from main lumen 206 to external pressure transducer 118 so that blood pressure can be determined using a method that is known to those of ordinary skill in the art. Conducting wire 202 exits member 102 through an exit point 208. Exit point 208 is sealed with an adhesive or a polymeric material. Conducting wire 202 is electrically coupled to cable 114 by a joint 210. This joint can be made by soldering, or another wire joining method known to people of ordinary skill in the art. Cable 114 terminates with a connector 116 that can mate with either the generator 122, or a separate extension connector cable (not shown). Cable 114 and connector 116 are made of materials suitable for sterilization, and will insulate the user from energy travelling through the conductor.

Member 102 is coupled to tubing 212 at proximal end 214 of member 102. Tubing is made of a polymeric material that is more flexible than member 102. A suitable material for tubing is polyvinylchloride (PVC), or another flexible polymer. Tubing 212 is coupled to hub 112. This configuration provides a flexible region for the user to handle when releaseably coupling external pressure transducer 118, or other devices to hub 112. Couplings between member 102 and tubing 212, and tubing 212 and hub 112 are made with an adhesive such as a UV curable adhesive, an epoxy, or another type of adhesive.

A housing 216 surrounds joint 210 and proximal end of member 102 in order to conceal these connections. Housing is made of a polymeric material, and is filled with a filling agent 218 such as an epoxy, or another polymeric material in order to hold cable 114 and tubing 212 in place.

Figure 4:
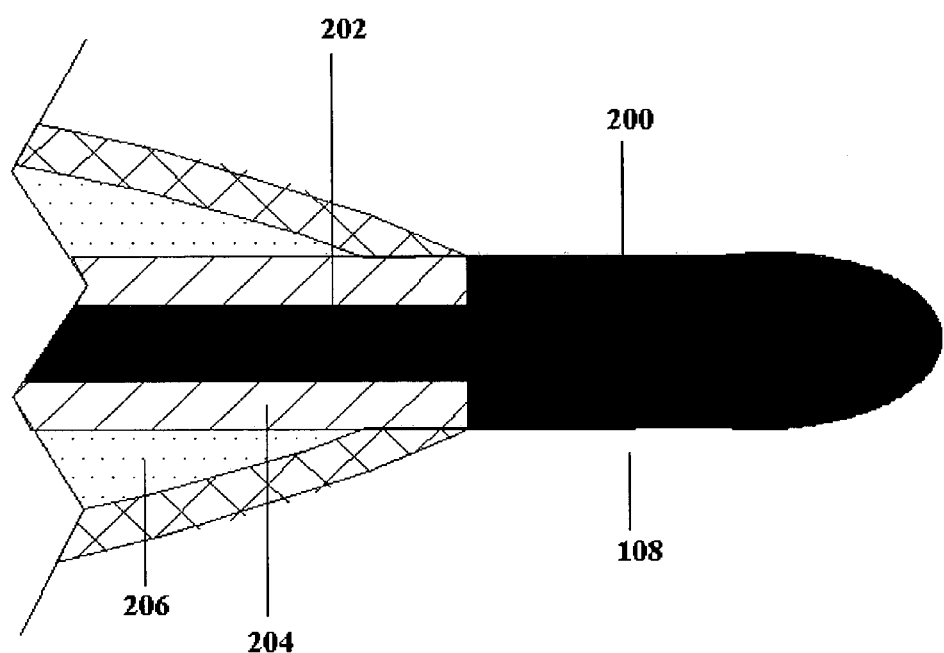
FIG. 4 illustrates an active electrode of the device of FIG. 1.

Referring to FIG. 4 there is illustrated a view of a preferred embodiment of functional tip 108. Functional tip 108 comprises one active electrode 200 configured in a bullet shape. Active electrode 200 is preferably 0.059" (0.15 cm) long and preferably has an outer diameter of 0.016" (0.04 cm). Active electrode 200 is coupled to an end of conducting wire 202, also made out of a conductive and radiopaque material. RF energy is delivered through active electrode 200 to tissue, and travels through the patient to grounding pad 124, which is connected to generator 122. Alternate embodiments of active electrode 200 are configured in shapes other than a bullet. These shapes include a spherical shape, a rounded shape, a ring shape, a semi-annular shape, an ellipsoid shape, an arrowhead shape, a spring shape, a cylindrical shape, among others.

Figure 5:
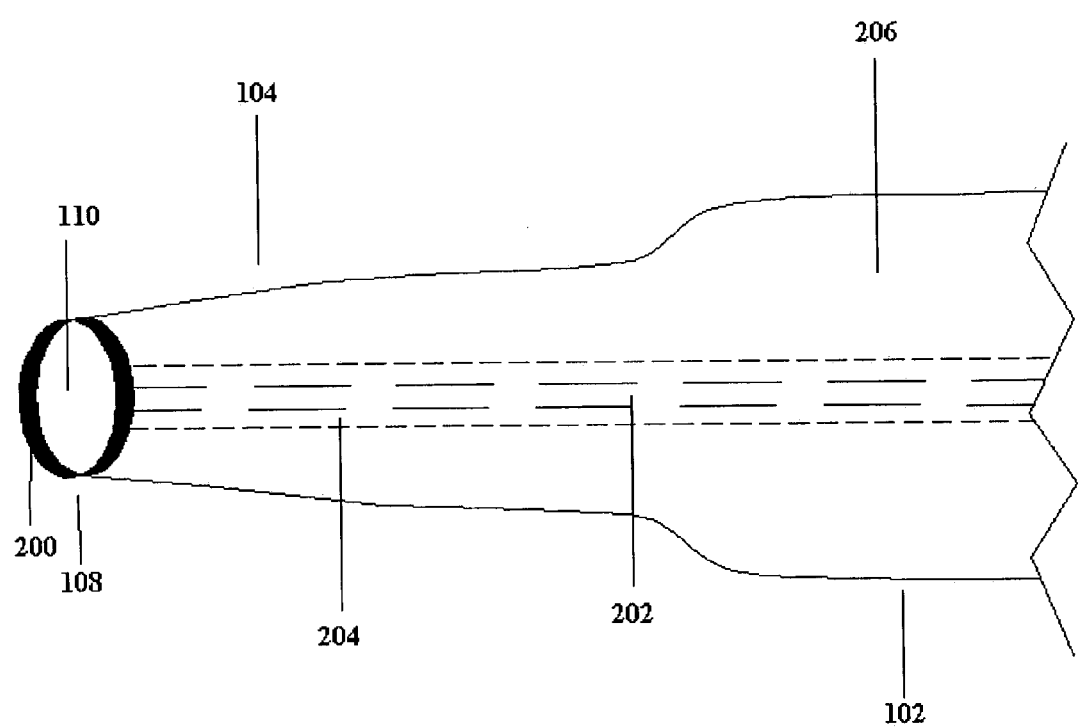
FIG. 5 illustrates an alternate embodiment of the distal region of a device in accordance with the invention.

Referring to FIG. 5 there is illustrated an alternate embodiment of functional tip 108. Functional tip 108 comprises one active electrode 200 in a ring configuration. Conducting wire 202 is coupled to the active electrode 200, and active electrode 200 is positioned around a perimeter of a single opening 110 that provides a pathway between main lumen 206 and a patient's body. Another similar embodiment to functional tip 108 comprises an active electrode 200 in a partially annular shape (not shown). In other embodiments (not shown), functional tip 108 comprises multiple electrodes 200. Such electrodes 200 may operate in a monopolar mode as with the embodiments detailed in FIGS. 2 and 5. Otherwise, such electrodes 200 are arranged such that the RF energy is delivered through at least one active electrode at functional tip 108, and returns to the generator through at least one return electrode at functional tip 108. The use of an active and a passive electrode on board device 100 eliminates the need for a grounding pad 124 to be attached to the patient as is well understood by persons of ordinary skill in the art.

In the preferred embodiment, external pressure transducer 118 is releaseably coupled to device 100. Hub 112 is coupled to external tubing 119 that is coupled to external pressure transducer 118 as shown in FIG. 1. External tubing 119 is flushed with saline to remove air bubbles. When device 100 is positioned in a blood vessel in a body, pressure of fluid at distal region 104 exerts pressure through openings 110 on fluid within main lumen 206, which exerts pressure on saline in external tubing 119, which exerts pressure on external pressure transducer 118. The at least one opening 110 and lumen 206 provide a pressure sensing mechanism in the form of a pressure transmitting lumen for coupling to pressure transducer 118. External pressure transducer 118 produces a signal that varies as a function of the pressure it senses. External pressure transducer 118 is also releaseably electrically coupled to a pressure monitoring system 120 that converts the transducer's signal and displays a pressure contour as a function of time.

Figure 6:
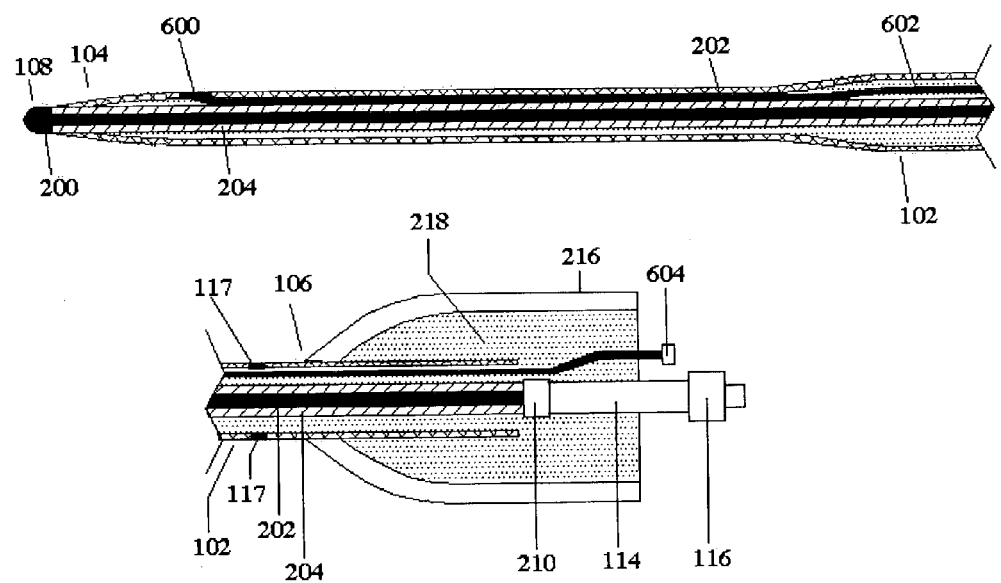
FIG. 6 illustrates a side cross-sectional view of an alternate embodiment of the device.

Referring to FIG. 6 there is illustrated an alternate embodiment of device 100 that does not use an external pressure transducer. In this embodiment the pressure sensing mechanism comprises an on-board pressure transducer 600 coupled by an adhesive to elongate member 102 at distal region 104. Pressure transducer 600 is configured at distal region 104 such that pressure close to functional tip 108 can be transduced. On-board pressure transducer 600 is electrically coupled to a pressure communicating cable 602 to provide power to transducer 600 and to carry a pressure signal to proximal region 106 of device. Pressure communicating cable 602 terminates in a monitoring system connector 604 that is configured to be releaseably coupled to pressure monitoring system 120. Monitoring system 120 converts the pressure signal and displays pressure as a function of time. In the embodiment of FIG. 6, a main lumen is not required for fluid communication with an external pressure transducer. In addition, this embodiment does not require openings at distal region 106 for fluid communication with a main lumen. However, a lumen with openings may be provided for injecting or aspirating fluids, if desired.

Figure 7:
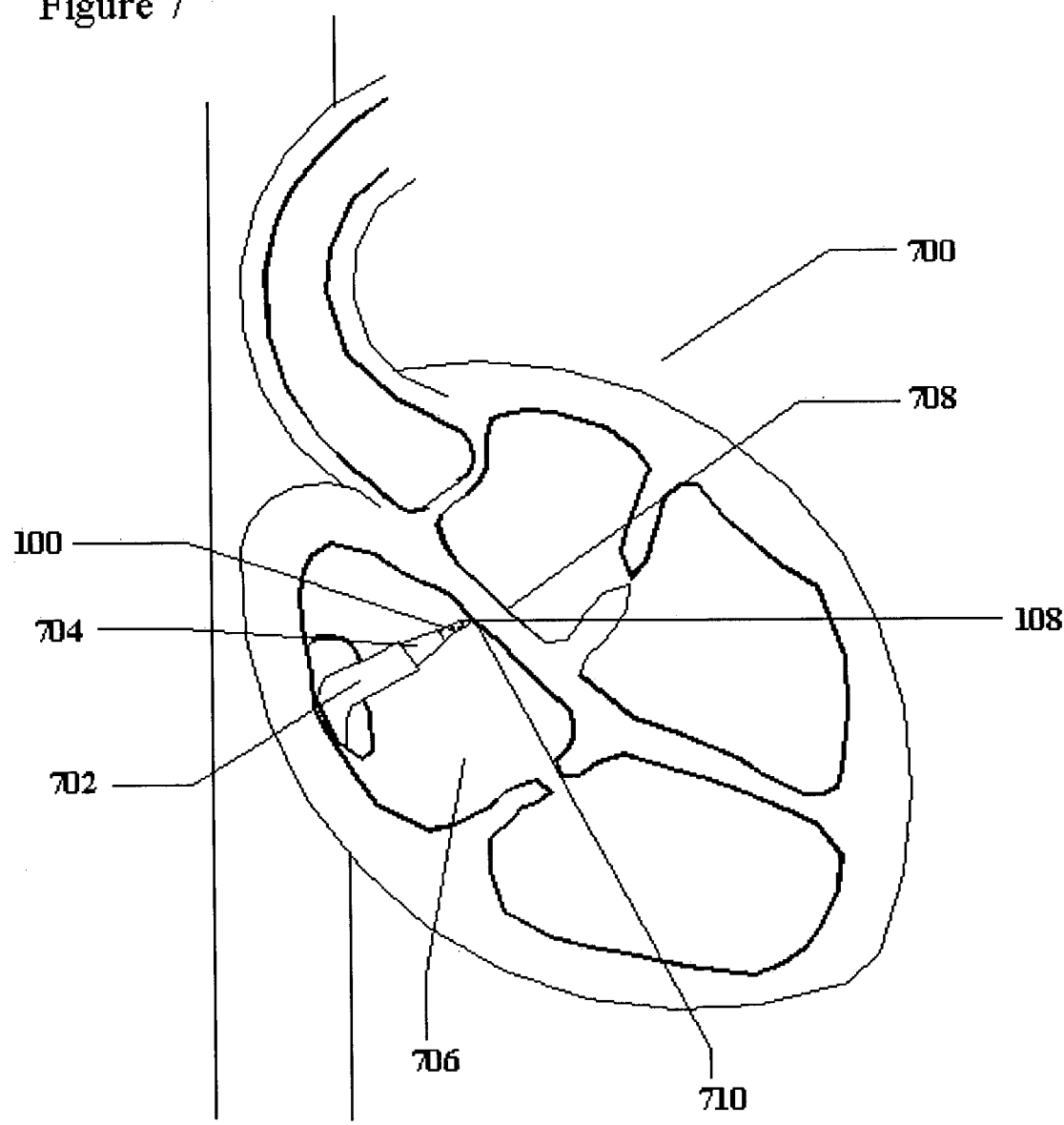
FIG. 7 illustrates a first position of the device of FIG. 1 against an atrial septum of a heart.
Figure 8:
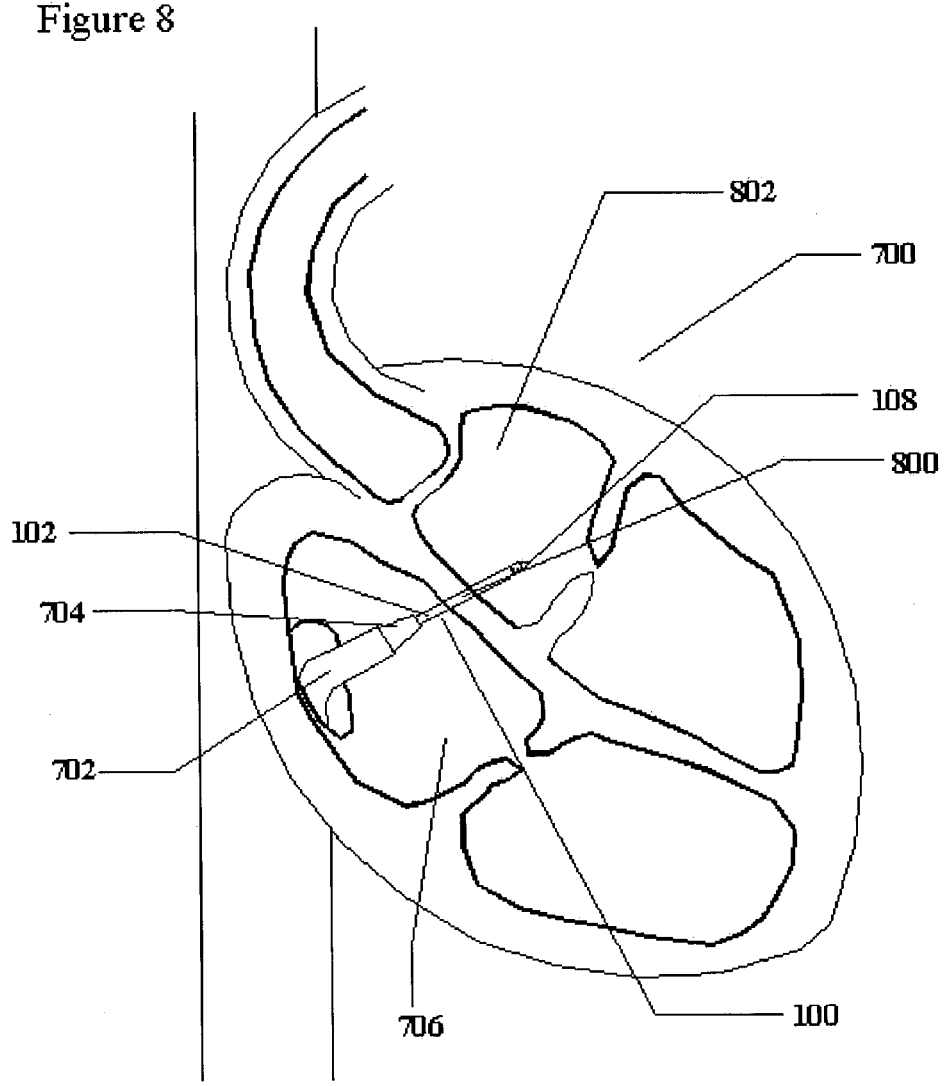
FIG. 8 illustrates a second position of the device of FIG. 1, after successful perforation of the atrial septum.
Figure 9:
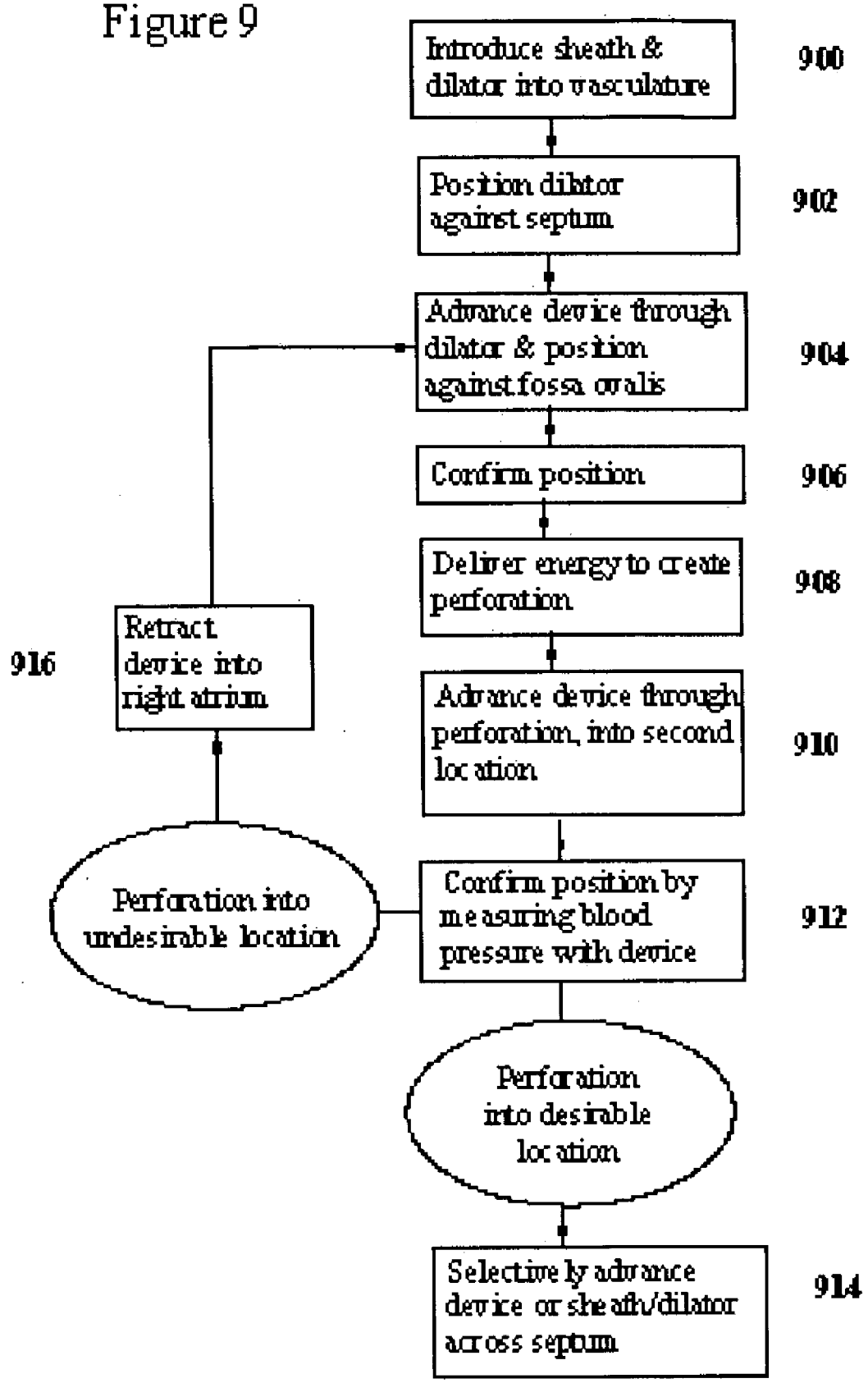
FIG. 9 illustrates a flow chart of a transseptal perforation method in accordance with this invention.

Device 100 of this invention can be used for general electrosurgery in instances where it is desirable to cut tissue or other material and simultaneously determine blood pressure. More specifically, it can be used for creating a perforation such as a transseptal perforation. Referring to FIGS. 7 and 8 there is illustrated device 100 within a heart 700 of a patient. A method for creating a transseptal perforation is outlined in flow chart form in FIG. 9. In accordance with a method aspect of the invention for creating a transseptal perforation, a guiding sheath 702 and dilator set 704 with a lumen larger than the outer diameter of device 100 is introduced into a patient's vasculature (step 900). Guiding sheath 702 and dilator 704, known to those of ordinary skill in the art, are advanced together and positioned within a right atrium 706 of heart 700 so that the tip of dilator 704 is positioned against atrial septum 708, as shown in FIG. 7 (step 902).

Once dilator 704 is in position, device 100 is advanced through dilator 704 and functional tip 108 is positioned against fossa ovalis 710, a preferred first desired location on atrial septum 708 to create a perforation (step 904). Device 100 is coupled to external pressure transducer 118 and a right atrial pressure contour, known to those of ordinary skill in the art, is shown on monitoring system 120. The technique for obtaining a pressure contour was previously described. The position of functional tip 108 may be additionally confirmed using an imaging modality such as fluoroscopy (step 906). Once the position is confirmed, generator 122 is activated and RF energy is' delivered through device 100 to make perforation 800 (step 908).

Device 100 is thereafter advanced through perforation 800 and into a second location (step 910). The desirability of the position of perforation 800 is confirmed through imaging techniques in combination with the evaluation of the pressure contours from the pressure transducer (step 912). The preferred second location is left atrium 802 of the heart. Device 100 remains coupled to external pressure transducer 118 so that a pressure contour at the second location can be monitored.

After successful perforation a left atrial pressure contour, known to those of ordinary skill in the art, will be shown on the monitoring system. If perforation 800 is successfully made in the correct location, member 102 may be further advanced through perforation 800 if required (step 914). In some cases further advancement of device 100 is not necessary as guiding sheath 702 and dilator 704 can be advanced through perforation 800 without further advancing device 100. In the event that the imaging and pressure readings show that the perforation 800 is made in an undesirable location, device 100 is retracted into the right atrium 706 (step 916) and is repositioned for another perforation attempt.

The present invention thus provides a device that is capable of creating a controlled perforation while determining a position of the device in response to pressure at a location in the body. The controlled perforation is created by the application of energy by a generator to a functional tip on the device. A means for determining the position of the device may comprise a pressure transmitting lumen that can be releasably coupled to an external pressure transducer. In this embodiment, there is at least one opening near the distal region of the device for blood or other fluid to enter and fill the lumen and exert a measurable pressure on a coupled external transducer. The lumen and opening may also be useful for injecting radiopaque contrast or other agents through the device. In an alternate embodiment, the means for determining a position of the device in response to pressure comprises a transducer located on the device proximal to the functional tip.

The device of the invention is useful as a substitute for a traditional transseptal needle to create a transseptal perforation. The device of the present invention preferably has a soft distal region with a functional tip that uses RF energy to create a perforation across a septum, making the procedure more easily controlled and less operator dependent than a transseptal needle procedure. The soft distal region of the device reduces incidents of vascular trauma as the device is advanced through the vasculature. The application of RF energy is controlled via an electric generator, eliminating the need for the operator to subjectively manage the amount of force necessary to cross the septum with a traditional needle. The present invention eliminates the danger of applying too much mechanical force and perforating the posterior wall of the heart.

The present invention also provides a method for the creation of a perforation in an atrial septum. Pressure monitoring is particularly important in this procedure, as there is the possibility of inadvertently perforating the aorta due to its proximity to the atrial septum. Pressure measurements allow the operator to confirm that the distal end of the device has entered the left atrium, and not the aorta, or another undesirable location in the heart. Preferably, the device will also be visible using standard imaging techniques, however the ability to monitor pressure provides the operator with a level of safety and confidence that would not exist using only these techniques.

While the surgical device thus described is capable of cutting living tissue, it will be understood by persons of ordinary skill in the art that an appropriate device in accordance with the invention will be capable of cutting or removing material such as plaque or thrombotic occlusions from diseased vessels as well.

Although the above description relates to specific embodiments as presently contemplated by the inventors, it is understood that the invention in its broad aspect includes mechanical and functional equivalents of the elements described herein.

What is claimed is:

1. A surgical device for perforating material and monitoring pressure comprising:
   an elongate member having a distal region with a first outer diameter and a proximal region with a second outer diameter larger than said first outer diameter such that dilation of a perforation is limited while said distal region is advanced through said perforation, wherein said second outer diameter tapers down to said first outer diameter so as to provide a smooth transition between said first outer diameter and said second outer diameter;
   an energy delivery device associate with said elongate member at said distal region, said energy delivery device adapted for connection to an energy source and operable to effectively perforate said material by delivering energy; and
   a pressure sensing mechanism associated with said distal region for monitoring pressure about said distal region;
   wherein said pressure sensing mechanism comprises a pressure transmitting lumen extending between said proximal and distal regions, the lumen at said proximal region being adapted for fluid communication with a pressure transducer that provides a signal which varies as a function of pressure and adapted at said distal region for fluid communication with an environment about said distal region.

2. The device as claimed in claim 1, wherein said energy is at least one form of energy selected from a group consisting of: electrical current; microwave; ultrasound; and laser.

3. The device as claimed in claim 2 wherein said electrical current has a frequency within the radio frequency range.

4. The device as claimed in claim 1 wherein said material comprises cellular tissue and wherein said energy delivery device is operable to deliver sufficient energy to the tissue to result in a rapid increase in the intracellular temperature causing vaporization of intracellular water and subsequent cell lysis.

5. The device as claimed in claim 1 wherein said distal region comprises at least one opening to the environment and wherein said lumen is in fluid communication with said at least one opening.

6. The device as claimed in claim 1 wherein said energy delivery device comprises a functional tip with at least one active electrode.

7. The device as claimed in claim 6 wherein said at least one electrode comprises an active electrode with an outer diameter of substantially 0.04 cm.

8. The device as claimed in claim 1 wherein said energy delivery device comprises a functional tip having two or more electrodes.

9. The device as claimed in claim 8 wherein the electrodes are configured in an arrangement where at least one of said electrodes is active and at least one is a return electrode.

10. The device as claimed in claim 1 wherein said surgical device comprises a radiopaque marker.

11. A method of surgery comprising the steps of:
(i) introducing a surgical device into a body of a patient, said surgical device comprising a flexible elongate member having a distal region and a proximal region, an energy delivery device capable of perforating material and a pressure sensing mechanism for determining pressure in the body, said energy delivery device and pressure sensing mechanism associated with said distal region;
(ii) positioning said surgical device to a first desired location in the patient's body where said energy delivery device is adjacent the material to be perforated;
(iii) creating a perforation in said material by delivering energy using said energy delivery device; and
(iv) measuring pressure in said body using said pressure sensing mechanism in order to determine a position of said surgical device at least one of before and after step (iii);
wherein said material is tissue located on an atrial septum of a heart.

12. The method as claimed in claim 11 further comprising the step of:
(v) advancing said surgical device through said perforation to a second desired location.

13. The method as claimed in claim 12 further comprising the step of:
(vi) measuring pressure using the pressure sensing mechanism at the second location.

14. The method of claim 12 wherein pressure is measured both at said first desired location and at said second desired location.

15. The method of claim 12 wherein said first desired location and said second desired location are at different pressures such that a pressure measurement at said first desired location produces a first pressure contour and a pressure measurement at said second desired location produces a second pressure contour, wherein said first pressure contour and said second pressure contour are different.

16. The method as claimed in claim 11 wherein step (i) comprises introducing said surgical device into said patient's vasculature.

17. The method as claimed in claim 16 wherein the step of introducing said surgical device into said patient's vasculature comprises inserting said surgical device into a guiding catheter positioned in said patient's vasculature.

18. The method as claimed in claim 11, further comprising the step of advancing said surgical device through said perforation to a second desired location wherein the second location is a left atrium.

19. The method as claimed in claim 11 further comprising a step of determining a position of the device using fluoroscopic imaging and wherein said surgical device comprises a radiopaque marker.

20. The method as claimed in claim 11 wherein said first desired location is a fossa ovalis of said patient's heart.

21. The method of claim 11 wherein pressure is measured after said perforation is created.

22. An electrosurgical device comprising:
a flexible elongate member having a distal region and a proximal region, said distal region insertable within and along a lumen within a body of a patient and maneuverable therethrough to a desired location where the device is opoerable to perforate material and monitor pressure at said desired location;
at least one active electrode associated with said distal region for perforating said material, said at least one active electrode having an outer diameter of substantially 0.04 cm and adapted for coupling to an electrical power source; and
a pressure sensing mechanism associated with said distal region for sensing pressure at said desired location, the mechanism adapted for coupling to a pressure monitoring system;
wherein said pressure sensing mechanism comprises a pressure transmitting lumen defined within the elongate member extending from said proximal region to and through at least one opening defined in said distal region.

23. The device as claimed in claim 22 wherein said pressure sensing mechanism is configured to minimize a portion of the elongate member that is necessary to be located at said desired location to monitor pressure.

24. The device as claimed in claim 22 wherein said proximal region is adapted for coupling said pressure transmitting lumen to a pressure transducer associated with said pressure monitoring system.

25. The device as claimed in claim 22 wherein said pressure transmitting lumen is adapted for at least one of injecting a fluid to or removing a fluid from said body.

26. The device as claimed in claim 22 wherein said at least one active electrode is coupled to said electrical power source by a coupling means extending through said pressure transmitting lumen.

27. The device as claimed in claim 22 wherein said at least one active electrode defines a functional tip comprising a conductive and radiopaque material at said distal region.

28. The device as claimed in claim 27 wherein said electrical power source is capable of providing a high-frequency electrical power to said functional tip in a high impedance range.

29. The device as claimed in claim 22 wherein said device comprises a radiopaque marker.

30. The device as claimed in claim 22 wherein said distal region has a first outer diameter and said proximal region has a second outer diameter and wherein said first outer diameter is smaller than said second outer diameter such that dilation of a perforation is limited while said distal region is advanced through said perforation.

31. The device as claimed in claim 30 wherein said second outer diameter tapers down to said first outer diameter so as to provide a smooth transition between said first outer diameter and said second outer diameter.

32. A method of perforating material at a desired location in a body of a patient comprising the steps of:
  inserting a surgical device into said body, said surgical device comprising means for perforating material and means for determining a position of the device responsive to pressure within said body;
  positioning said surgical device at said desired location in response to said means for determining a position of the device; and
  perforating material at said desired location.

33. The method as claimed in claim 32 comprising the step of: advancing said device in said body in response to said means for determining a position of the device.

34. The method as claimed in claim 33 comprising re-positioning said device for perforating in response to said means for determining a position of the device.

35. A method of surgery comprising the steps of:
  (i) introducing a surgical device into a body of a patient, said surgical device comprising a flexible elongate member having a distal region and a proximal region, an energy delivery device capable of perforating material and a pressure sensing mechanism for determining pressure in the body, said energy delivery device and pressure sensing mechanism associated with said distal region;
  (ii) positioning said surgical device to a first desired location in the patient's body where said energy delivery device is adjacent the material to be perforated;
  (iii) creating a perforation in said material by delivering energy using said energy delivery device;
  (iv) advancing said surgical device through said perforation to a second desired location; and
  (v) measuring pressure in said body using said pressure sensing mechanism in order to determine a position of said surgical device at least one of before and after step (iii).

36. The method as claimed in claim 35 further comprising the step of:
  (vi) measuring pressure using the pressure sensing mechanism at the second location.

37. The method of claim 35 wherein pressure is measured both at said first desired location and at said second desired location.

38. The method of claim 35 wherein said first desired location and said second desired location are at different pressures such that a pressure measurement at said first desired location produces a first pressure contour and a pressure measurement at said second desired location produces a second pressure contour, wherein said first pressure contour and said second pressure contour are different.

* * * * *